United States Patent [19]

Dockner et al.

[11] 3,957,874
[45] May 18, 1976

[54] CONTINUOUS PRODUCTION OF N-ALKYLARYLAMINES

[75] Inventors: Toni Dockner, Meckenheim; Herbert Krug, Ludwigshafen, both of Germany

[73] Assignee: BASF Aktiengesellschaft, Ludwigshafen (Rhine), Germany

[22] Filed: July 10, 1974

[21] Appl. No.: 487,236

[30] Foreign Application Priority Data

July 14, 1973 Germany............................ 2335906

[52] U.S. Cl. ............................ 260/577; 260/465 E; 260/574
[51] Int. Cl.$^2$ ................. C07C 87/62; C07C 121/50
[58] Field of Search ................. 260/577, 574, 465 E

[56] References Cited
UNITED STATES PATENTS 2,991,311  7/1961  Thoma et al......................... 260/577

FOREIGN PATENTS OR APPLICATIONS 163,007  10/1933  Switzerland......................... 260/577

*Primary Examiner*—D. Horwitz
*Attorney, Agent, or Firm*—Johnston, Neil, Thompson & Shurtleff

[57] ABSTRACT

An improved process for the continuous production of N-alkylarylamines by reaction of arylamines with alkanols and/or dialkyl ethers in the gas phase at a temperature of from 180° to 450°C in the presence of carrier substances which contain an oxyacid of phosphorus. The improvement consists in using silicic acid having an internal surface area of from 50 to 500 square meters per gram and a content of from 0.1 to 20% by weight of phosphoric acid and in the continuous supply of phosphoric acid and/or an alkyl phosphate to the catalyst during the reaction. N-alkylarylamines are starting materials for the production of dyes, pesticides, plant protection agents and growth regulators. They are also suitable as additives to mineral oils or to coating compositions and other polymerized systems.

9 Claims, No Drawings

CONTINUOUS PRODUCTION OF N-ALKYLARYLAMINES

This invention relates to an improved process for the continuous production of N-alkylarylamines by the reaction of an arylamine with an alkanol and/or dialkyl ether in the gas phase at a temperature of from 180° to 450°C in the presence of a carrier substance which contains an oxyacid of phosphorus.

The reaction of arylamines with alkanols or dialkyl ethers for the production of N-alkyl derivatives of aromatic amines is a process which has been introduced into industry. The catalysts used are as a rule substances which have neither predominantly dehydrating properties nor predominantly dehydrogenating properties. Examples of suitable catalysts are aluminum oxide and silicates. Non-aged aluminum oxide is used in the process described in German Pat. No. 693,417 and silicic acid, for example TONSIL, is used in the process described in German Pat. No. 638,756 as the catalyst. Both aluminum oxide and silicic acid, for example TONSIL, have the disadvantage in the alkylation of aromatic amines that their activity rapidly subsides and therefore their life is very limited (cf. Houben-Weyl, "Methoden der organichen Chemie", volume XI/1, page 116, and J. Amer. Chem. Soc., volume 46 (1924), page 1838). It is also known from German Patent 617,990 that carrier substances having a content of an oxyacid of phosphorus or a salt thereof may be used as catalysts in the reaction of aromatic amines with alkanols. These catalysts do not however reach the standard as regards life required by industry.

It is an object of the invention to provide a process in which high yields and good conversions are achieved. It is another object of the invention to provide a process in which the catalysts used retain their activity for a longer period than hitherto. Finally it is an object of the invention to provide a process in which scarcely any nuclear alkylation takes place.

In accordance with this invention these and other objects and advantages are achieved in an improved process for the continuous production of an N-alkylarylamine by the reaction of an arylamine with an alkanol and/or a dialkyl ether in the gas phase at a temperature of from 180° to 450°C in the presence of a carrier substance which has a content of an oxyacid of phosphorus wherein the improvement comprises using as the catalyst a silicic acid having an internal surface area of from 50 to 500 square meters per gram and a content of from 0.1 to 20% by weight of phosphoric acid and continuously supplying phosphoric acid and/or an alkyl phosphate to the catalyst during the reaction.

It is preferred to use aromatic amines of the formula:

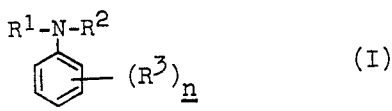

in which
R[1] and R[2] may be hydrogen;
R[1] may also be alkyl of one to four carbon atoms;
R[3] may be hydrogen, cyano or nitro or alkyl or alkoxy of up to four carbon atoms;
n is 1 or 2;
R[3] may also be phenyl or the radical of the formula:

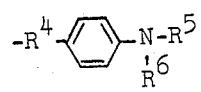

in which R[4] is alkylene or alkylidene of up to three carbon atoms;
R[5] is hydrogen or alkyl of one to four carbon atoms;
R[6] is hydrogen, and
n is 1 if R[5] is $C_{1-4}$ alkyl.

It is preferred to start from an aromatic amine which is derived from benzene and has one amino group. In addition to the amino group the preferred aromatic amines may contain one or two substituents which are inert under the reaction conditions such as alkyl of one to four carbon atoms, alkoxy of one to four carbon atoms, cyano, nitro or halogen. Anilines and toluidines are particularly preferred as starting materials. Examples of suitable amines are aniline, o-toluidine, m-toluidine, p-toluidine, anisidines, nuclear halogenated anilines, m-nitroaniline, p-nitroaniline and 4,4-diaminodiphenylmethane.

Preferred alkanols are those of one to four carbon atoms such as methanol, ethanol, propanol, isopropanols or butanols. Methanol and ethanol have achieved special significance. Suitable dialkyl ethers are those having dialkyl radicals of one to four carbon atoms. Ethers with identical alkyl radicals are particularly preferred. Examples of suitable ethers are dimethyl ether, diethyl ether, di-n-propyl ether, diisopropyl ether and dibutyl ether. Dimethyl ether and diethyl ether have achieved particular importance.

Naturally the preferred end products result from the preferred starting materials. When the starting material is an alkylarylamine, a tertiary amine is obtained. If it should be preferred to produce monoalkylamines the starting materials are conveniently primary amines. On the other hand it is possible to return monoalkylarylamines or dialkylarylamines formed as byproducts to the reaction where they are further alkylated or in the case of dialkylarylamines converted into monoalkylarylamines.

It is advantageous to use from 1 to 4 moles of alkanol or dialkyl ether per mole of aromatic amine. When it is desired to prepare an N-dialkylarylamine it has proved to be advantageous to use from 1 to 3 moles of alkanol or dialkyl ether per mole of aromatic amine.

The reaction is carried out at a temperature of from 180° to 450°C. Particularly good results are obtained at temperatures of from 220° to 350°C. The reaction is carried out as a rule at atmospheric pressure. It is also possible to use slightly superatmospheric pressure, for example of up to 10 bar. The reaction is moreover carried out in the gas phase. The temperature and pressure conditions are naturally chosen so that a gas phase is present. It has additionally proved to be advantageous to make use of carrier gases which are inert under the reaction conditions such as nitrogen.

Silicic acid having an internal surface area of from 50 to 500 square meters per gram and a content of from 0.1 to 20% by weight of phosphoric acid is used as the catalyst. Silicic acid which has an internal surface area of from 300 to 450 square meters per gram and a content of from 2 to 10% by weight of phosphoric acid based on the total weight of the catalyst has proved to be particularly suitable. The internal surface area of the silicic acid is determined for example by the BET method.

Suitable catalysts are obtained for example according to the methods described in Ullmann's Enzyklopadie der technischen Chemie, 3rd edition, volume 9, pages 275 et seq. Suitable catalysts may be prepared with particular advantage for example by adding aqueous mineral acid, for example from 20 to 35% by weight sulfuric acid, for example to a sodium waterglass solution having a density of from 1.15 to 1.20 g/ccm and converting it via the intermediate stage of a silicic acid sol into a water-rich silicic acid hydrogel which is washed with ammoniacal water, for example from 0.1 to 0.2% by weight ammonia solution. The hydrogel thus freed from salt is treated with the necessary amount of phosphoric acid, advantageously with the addition of oxalic acid, for example from 5 to 15% based on silicic acid, in a mill or other apparatus producing shear forces so that peptization takes place. The substance thus obtained is sprayed for example into a stream of smoke gas so that a granular powder suitable as a fluidized bed catalyst is obtained or is converted into catalyst moldings by a conventional method.

It is a special feature of the invention that phosphoric acid and/or an alkyl ester of phosphoric acid is supplied continuously during the reaction. It is convenient to pass phosphoric acid and/or an alkyl ester of phosphoric acid dissolved in the alkanol or dialkyl ether used into the bed of catalyst. It is preferred to use a trialkyl ester of phosphoric acid, particularly with alkyl radicals of one to four carbon atoms and the alkyl radicals preferably correspond to those of the alkanol or dialkyl ether used in each case. It has proved to be particularly advantageous for 0.1 to 5 g of phosphoric acid or alkyl phosphate to be supplied per liter of catalyst per hour. Suitable alkyl phosphates include trimethyl phosphate, triethyl phosphate, tripropyl phosphate or triisobutyl phosphate. When trialkyl phosphates are used it is also possible to vaporize these together with the aromatic amines and alkanols or dialkyl ethers used.

It has also proved to be advantageous to maintain a residence time of from four to twenty seconds at the catalyst. Particularly good results are also obtained when from 100 to 800 g of aromatic amine is used per liter of catalyst per hour.

The process according to the invention may be carried out for example by vaporizing the said aromatic amine, alkanol and/or dialkyl ether and passing the starting materials in gas phase, with or without an inert gas and, when an alkyl phosphate is used, with the addition of the same over a stationary or fluidized bed of catalyst of the said composition. Phosphoric acid dissolved in the alkanol may also be introduced into the bed of catalyst if desired. The stated temperatures, residence times and the said space velocity are all maintained. The reaction mixture thus obtained is either condensed or supplied direct as gas to a fractionating column, the N-alkylarylamine being obtained in pure form. Unreacted alkanol, dialkyl ether and aromatic amine may be returned to the reaction.

N-alkylarylamines which are prepared according to the process of the invention are starting materials for the production of dyes, pest control agents or other biological active ingredients such as plant protection agents and growth regulators. They are also suitable as additives to mineral oils and to surface coating compositions and other polymerized systems.

The process according to the invention is illustrated in the following Examples.

The parts given in the Examples are by weight. They bear the same relation to parts by volume as the kilogram to the liter.

EXAMPLE 1

50 parts of catalyst is located in a fluidized bed reactor having a capacity of 400 parts by volume. The catalyst consists of silicic acid having an internal surface area of 400 square meters per gram and has a content of 10% by weight of phosphoric acid. 45 parts of a mixture of 11.1% by weight of aniline and 88.9% by weight of ethanol (molar ratio 1:16) is vaporized per hour at 240°C in a quartz vaporizer provided beneath the fluidization zone and is passed upwardly into the fluidization zone. The fluidized zone is kept at a temperature of 300°C during the reaction. At the same time 5 parts of a mixture of 0.7% by weight of phosphoric acid and 99.3% by weight of ethanol is passed direct into the fluidized bed. The residence time is 6.5 seconds. The gaseous reaction mixture obtained is then condensed. The hourly yield is 48 parts of condensate which contains 0.25 part of aniline, 1.5 parts of N-monoethylaniline and 5.6 parts of N,N diethylaniline. This is equivalent to a conversion of 95%. 73.5% of the aniline reacted is converted into N,N-diethylaniline and 23.5% into N-monoethylaniline.

EXAMPLE 2

The procedure described in Example 1 is repeated but the mixture vaporized is 55 parts of 54.5% by weight of aniline and 45.5% by weight of methanol (molar ratio 1:2.4) and the fluidized bed is kept at a temperature of 330°C. The residence time is 6.5 seconds. After a similar procedure the hourly yield is 54 parts of condensate which contains (besides 2.1 parts of aniline) 25.2 parts of N-monomethylaniline having a boiling point of 196°C at 760 mm and 7 parts of N,N-dimethylaniline having a boiling point of 194°C at 760 mm.

This is equivalent to a conversion of 93%.

The yield of N-methylaniline and N,N-dimethylaniline is 97.8%.

EXAMPLE 3

The procedure described in Example 1 is repeated but 110 parts of a mixture of 66% by weight of o-toluidine, 34% by weight of ethanol (molar ratio 1:1.2) and 0.03% by weight of triethyl phosphate is used which is vaporized at 250°C while the fluidized bed is heated to a temperature of 330°C. 108 parts of condensate is obtained per hour.

The condensate contains 14.5 parts of o-toluidine with 60.0 parts of N-monoethyltoluidine and 10.7 parts of N,N-diethyl-o-toluidine. The conversion is 80%. Of the o-toluidine reacted 82.5% is converted into N-monoethyltoluidine and 13.1% into N,N-diethyltoluidine.

After 1000 hours the conversion is unchanged at 80%. The catalyst then has a carbon content of less than 0.5% by weight. 5% of the ethanol used is obtained as ethylene.

EXAMPLE 4

The procedure described in Example 1 is repeated but 115 parts of a mixture of 41.8% by weight of o-toluidine, 10.4% by weight of N,N-diethyltoluidine and 47.8% by weight of ethanol is used which is vaporized at 250°C while the fluidized bed is heated to a temperature of 330°C. At the same time 5 parts of a mixture of 0.7% by weight of phosphoric acid is passed direct into the fluidized bed. 116 parts per hour of a condensate is obtained which contains 11.10 parts of o-toluidine, 44.60 parts of N-monoethyltoluidine and 12 parts of N,N-diethyltoluidine.

The conversion is 77%. Of the reacted o-toluidine 96% is converted into N-monoethyltoluidine. The conversion is unchanged after 1000 hours.

We claim:

1. In a process for the continuous production of N-alkylarylamine by the reaction of an arylamine with an alkanol or a dialkyl ether in the gas phase at a temperature of from 180° to 450°C. in the presence of a carrier substance containing an oxyacid of phosphorus, the improvement which comprises reacting said arylamine with an alkanol of one to four carbon atoms or a dialkyl ether of one to four carbon atoms in each alkyl and using as the catalyst a silicic acid having an internal surface area of from 50 to 500 square meters per gram and having a content of from 0.1 to 20% by weight of phosphoric acid and continuously supplying phosphoric acid or an alkyl phosphate to the catalyst during the reaction.

2. A process according to claim 1 wherein from 1 to 20 moles of alkanol or dialkyl ether is used per mole of arylamine.

3. A process as claimed in claim 1 wherein the silicic acid used has an internal surface area of from 300 to 450 square meters per gram.

4. A process as claimed in claim 1 wherein a silicic acid is used which contains from 2 to 10% by weight of phosphoric acid.

5. A process as claimed in claim 1 wherein from 0.1 to 5 g of phosphoric acid or an alkyl phosphate is supplied per hour to each liter of catalyst.

6. A process as claimed in claim 1 wherein the starting material is an aromatic amine of the formula:

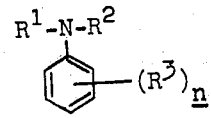

(I)

in which

R¹ is hydrogen or alkyl of one to four carbon atoms;
R² is hydrogen;
R³ is hydrogen, cyano, nitro or alkyl or alkoxy of up to four carbon atoms;
n is 1 or 2;
R³ may also be phenyl or the radical of the formula:

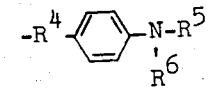

(II)

in which

R⁴ is alkylene or alkylidene of up to three carbon atoms;
R⁵ is hydrogen or alkyl of one to four carbon atoms;
R⁶ is hydrogen, and
n is 1 if R⁵ is C₁₋₄ alkyl.

7. A process as claimed in claim 1 wherein the starting material is an aromatic amine derived from benzene and having one amino group.

8. A process as claimed in claim 7 wherein the aromatic amine contains one or two substituents from the following group: alkyl of one to four carbon atoms, alkoxy of one to four carbon atoms, cyano, nitro or halogen.

9. A process as claimed in claim 1 wherein aniline or toluidine is used as the starting material.

* * * * *